(12) United States Patent
Sahatjian

(10) Patent No.: US 7,709,046 B1
(45) Date of Patent: May 4, 2010

(54) MEDICAL DEVICES COMPRISING NON CROSS-LINKED, THIN AND FLEXIBLE AQUEOUS COATINGS, AND METHODS RELATED THERETO

(75) Inventor: Ronald A. Sahatjian, Lexington, MA (US)

(73) Assignee: Medi-Solve Coatings, LLC., Natick, MA (US)

( * ) Notice: Subject to any disclaimer, the term of this patent is extended or adjusted under 35 U.S.C. 154(b) by 118 days.

(21) Appl. No.: 11/777,234

(22) Filed: Jul. 12, 2007

Related U.S. Application Data

(60) Provisional application No. 60/830,253, filed on Jul. 12, 2006.

(51) Int. Cl.
*B05D 3/02* (2006.01)
*B05D 1/00* (2006.01)
*B05D 1/18* (2006.01)
*H05H 1/00* (2006.01)
*A61M 25/00* (2006.01)
*A61B 1/01* (2006.01)

(52) U.S. Cl. .............. 427/2.1; 427/2.24; 427/2.25; 427/535; 427/536; 427/372.2; 427/429; 427/427.4; 427/430.1; 604/526; 604/164.13; 600/585; 600/144

(58) Field of Classification Search ......... 427/2.1–2.31, 427/535, 536, 372.2, 429, 427.4, 430.1; 600/585, 600/114; 604/526, 164.13
See application file for complete search history.

(56) References Cited

U.S. PATENT DOCUMENTS

| 4,925,445 | A | | 5/1990 | Sakamoto et al. |
| 5,069,226 | A | | 12/1991 | Yamauchi et al. |
| 5,091,205 | A | | 2/1992 | Fan |
| 5,620,738 | A | | 4/1997 | Fan |
| 5,702,754 | A | * | 12/1997 | Zhong ............... 427/2.12 |
| 5,722,424 | A | | 3/1998 | Engelson |
| 5,984,877 | A | * | 11/1999 | Fleischhacker, Jr. ...... 600/585 |
| 6,468,649 | B1 | * | 10/2002 | Zhong ............... 428/341 |
| 6,558,798 | B2 | * | 5/2003 | Zhong et al. .......... 428/420 |
| 6,709,706 | B2 | | 3/2004 | Zhong |
| 7,455,646 | B2 | | 11/2008 | Richardson et al. |

FOREIGN PATENT DOCUMENTS

EP 769306 A2 * 4/1997

OTHER PUBLICATIONS

Lewandowski et al. Dry Peelable Temporary Protective Coating waterbourne self-crosslinkable sulfourethane-silanol dispersions. 2004. Journal of Applied Polymer Science. vol. 91 pp. 1443-1449.*

* cited by examiner

*Primary Examiner*—Timothy H Meeks
*Assistant Examiner*—Cachet I Sellman
(74) *Attorney, Agent, or Firm*—IP Law Services, LLC.; Lucy Elandjian

(57) ABSTRACT

Disclosed are medical devices comprising a coil, coated with a multi-layer coating system and possess the flexibility, lubricity and trackability desired in applications where such devices are utilized. The coating system comprises a non-hydrophilic polymer primer coat and a hydrophilic polymer topcoat. These coating materials do not comprise any cross-linkers or reactive functional groups, and do not require the use of a hazardous solvent. The multi-layer coating system is very thin; having a maximum dry thickness in the range of about 15 microns to about 40 microns. Also disclosed are methods for coating and using these medical devices. The coatings are applied at low temperatures, in an aqueous environment, and in such a way that the coil is coated discretely, without forming a thick layer between the coil portions. Such coating prevents substantial bridging between the loops of the coil, thus preventing the coil tip from being stiff or non-trackable.

12 Claims, No Drawings

MEDICAL DEVICES COMPRISING NON CROSS-LINKED, THIN AND FLEXIBLE AQUEOUS COATINGS, AND METHODS RELATED THERETO

CROSS REFERENCE TO RELATED APPLICATION

This is a non-provisional application claiming the benefit of and priority to US provisional patent application having Ser. No. 60/830,253, filed on Jul. 12, 2006, which is incorporated herein by reference.

TECHNICAL FIELD

The present invention relates generally to a medical device or a part of such a device intended for use in the human body, that is coated with thin and flexible aqueous coatings, and methods related thereto. Specifically, the present invention pertains to medical devices comprising a coil, such as guide wires and catheters, coated with a multi-layer coating system comprising a non-hydrophilic polymer and a hydrophilic polymer that do not contain cross-linkers or reactive functional groups, and methods related thereto.

BACKGROUND

Medical devices comprising a coil, such as guide wires and catheters, are generally formed of stainless steel and may comprise a plastic material, such as a polyurethane, polyamide, or polyolefin, etc. Some medical devices, such as guide wires having a coil tip, may comprise a jacket or sleeve of a polymeric material that is coated or extruded over the coiled portion so as to provide a surface to which any subsequent coatings can adhere, as well as to provide smoothness and uniformity to the surface.

In certain medical procedures, a catheter is typically inserted at a predetermined site, and a guide wire tip is inserted through the catheter so that the coil tip is protruding from the catheter. Then, the catheter with the guide wire is inserted percutaneously into the targeted body part, such as a blood vessel, and the catheter is further inserted through the vessel by using the guide wire as a leading and supporting guide. These operations produce friction and abrasive forces that apply to the surfaces of the medical device. Relatively high friction between the catheter and the guide wire not only prevents the guide wire from being inserted through the catheter, but also prevents the guide wire from being easily moved through the catheter, thus making it difficult to carry out subtle indwelling operations at the targeted vessel site. Sometimes, the guide wire cannot be withdrawn from the catheter, rendering the catheter lumen unusable despite the completion of the indwelling operation. This higher level of friction presents an issue to the design and construction of such devices, as a low level of frictional resistance between the catheter's inner surface and the guide wire is desirable in the intended applications.

Attempts have been made to apply low frictional resistance Teflon and silicone oil to the outer surface of guide wires in order to overcome such problems. However, application of silicone oil fails to retain lubricity because of immediate loss of silicone coatings. Further, frequent applications add to frictional resistance, also undesirably creating the problems mentioned above.

In certain guide wires, the flexibility of the tip of the guide wire is created by having a very thin core wire over which a very fine coil wire is wound to make a flexible tip. For example, a core wire for a 0.014 inch (in.) guide wire may taper down to a 0.010 in. and be coiled with a wire of dimension 0.002 in. to create a 0.014 in. tip. The flexibility of the tip is dependent upon these coils being able to flex independent of each other and not be bound together. Various coatings have been applied to coiled tip guide wires or catheters to obtain a flexible distil tip of the wire or catheter. However, most coatings involve cross-linking and/or covalent binding to the device or a portion thereof. Thus, such coatings often form a film over the loop portions of the coil and lock them together, thereby creating a stiff tip. Also, when these wires are used in the body, the coil eventually flexes and breaks the coating into fragments. This often results in undesirable pieces being broken off in the body, as well as yielding a ragged or jagged broken coating.

Hydrophilic polyurethane coatings have been applied directly on metal surfaces. However, commercial versions of this technology require cross-linking and thick layers (60-80 microns thick) in order to achieve adequate performance. In practice, the thick layer extends continuously around the coated metal substrate. These layers have good cohesive forces and thus appear to be tightly bound on the metal surface, even though these layers do not necessarily have good adhesion to the metal surface. One disadvantage of such coatings is that because the polyurethane and other plastic layers are so thick, the diameter of the underlying wire must be correspondingly diminished. This is especially troublesome on very fine wires, such as those used in coronary angioplasty or neurointerventional catheterization procedures. These wires have outer diameters of about 0.010 in. to about 0.014 in. Alternatively, low frictional materials, such as polytetrafluoroethylene coatings, have been used. Such materials have lower friction than metals and most other plastic materials, and they can be applied directly onto metallic substrates. Other materials, such as high density polyethylene have been tried, but the coefficients of friction are not low enough for these materials to be useful. Oils have been applied; although their coefficients of friction are low, such treatments are transient as they wear off during use.

Hydrogel coatings are known to provide a lubricious surface for insertable devices. However, metals and certain plastic materials, such as polyolefins, polyamides, silicones, polyesters, have inert surfaces and it is often difficult to achieve acceptable adhesion when applying coatings, including hydrogel coatings, over such surfaces.

A variety of lubricious or "slippery" coatings have been proposed for use on biomedical devices, such as catheters, guide wires, endotracheal tubes and implants, in order to reduce friction when the device is introduced through tissue, or into blood vessels, or into other parts of the anatomy. Common materials used in the art to provide lubricious coatings for biomedical devices include oil, silicone and polymeric materials, such as poly N-vinylpyrrolidone, hydrophilic polyurethanes, polyethylene oxide and polyacrylic acid. Among the most common materials used to provide lubricious coatings are hydrophilic polymers which are covalently bonded to the substrate with a binder polymer having reactive functional groups, e.g., isocyanate, aldehyde and epoxy groups. Although the use of such binder polymers having reactive functional groups is effective in providing lubricious coatings that have a high degree of abrasion resistance, such binder polymers are often highly reactive, toxic, require solvents, and typically require special handling techniques in order to avoid potential health, safety and environmental problems. Further, the polymeric coating often contains cross-linkers, which generally contain hazardous or potentially hazardous materials, such as isocyanates or aziridines. Moreover, the cross-linked polymers yield a rigid coating that makes the coil of the wires stiff and non-trackable.

Accordingly, there is a need for medical devices, such as coiled guide wires, having a lower frictional resistance surface which enables more subtle operation in a vessel, and which can be easily inserted into a catheter, and for new or improved and less toxic coating processes to facilitate such devices.

SUMMARY OF THE INVENTION

Current coated medical devices comprising a coil, such as guide wires and catheters, are produced such that they lack the requisite flexibility, causing the coating of the device coil to break off, often in the body. Further, these devices are typically coated with a primer and a polymeric top coat that may contain harmful materials. The primer often contains isocyanate layers that can be potentially harmful in the body, and uses solvents that are difficult to remove, while the polymeric top coat comprises a cross-linker and/or reactive functional group that generally contain hazardous materials, such as isocyanates, or aziridines.

In view of the above, there is a need for a medical devices comprising a coil, such as guide wires and catheters, coated with a lubricious, flexible and non-toxic coating, and methods related thereto.

It is, therefore, an aspect of the present invention to provide a medical device comprising a coil, coated with a multi-layer coating system that comprises a thin non-hydrophilic primer coat capable of adhering to the surface of the medical device or a portion thereof, and a thin hydrophilic polymeric coat, wherein the hydrophilic polymeric material does not form a cross-linked or reacted polymer film that rigidifies the device or a portion thereof, such as the tip.

It is another aspect of the present invention to provide a method for coating a medical device comprising a coil such that the coating is thin and follows the contours of the coil without substantially bridging the coil structure.

It is another aspect of the present invention to provide a method for coating a medical device comprising a coil with coating materials that are non-toxic and not contain cross-linkers, isocyantates or reactive functional groups, and that can be easily applied at low temperatures and in an aqueous environment.

It is another aspect of the present invention to provide a method for coating a medical device comprising a coil with a lubricious coating to ensure a high degree of coil flexibility.

It is another aspect of the present invention to provide a method of using medical devices comprising a coil and coated with a multi-layer coating system that comprises a hydrophilic polymer that does not form a cross-linked or reacted polymer film.

The present invention pertains to medical devices comprising a coil and coated with a multi-layer coating system that comprises a non-hydrophilic polymer (primer coat) and a hydrophilic polymer (top coat). The coating system may also comprise a middle coat, between the primer coat and the top coat, comprising a mixture of the non-hydrophilic polymer and the hydrophilic polymer. These polymeric coating materials do not comprise a cross-linker or any reactive functional groups. Further, neither of these coating materials requires the use of a hazardous solvent. These coating materials can be easily applied at low temperatures and in an aqueous environment. The resultant coating is very thin, having a total maximum dry thickness of about 30 microns, preferably, about 15 microns, for a dual coat (primer coat and top coat) system, and about 40 microns, preferably about 25 microns, for a tri-coat (primer coat, middle coat and top coat) system, the primer coat having a dry thickness in the range of from about 1 micron to about 10 microns, preferably, from about 1 micron to about 5 microns, the top coat having a dry thickness in the range of from about 2 microns to about 20 microns, preferably, from about 2 microns to about 10 microns, and the optional middle coating having a thickness in the range of from about 2 microns to about 10 microns, preferably, from about 5 microns to about 10 microns. The coating is applied to the coil of the medical device in such a way that the contour and topology of the coil are retained and the coil is coated discretely without forming a thick layer between loop portions of the coil. The discrete coil coating prevents substantial bridging between loop portions of the coil, so as to not cause the coil tip to become stiff or non-trackable. These coated medical devices provide the desired lubricity and flexibility such that the physician is to be able to maneuver the device and select the vessel into which he/she wants to gain access. The present invention also pertains to a method for coating said medical devices comprising a coil with the multi-layer coating system described herein.

In one embodiment of the present invention, a thin layer of a non-hydrophilic polymer composition (forming the primer coat) is applied to the surface of a guide wire coil, and dried at room temperature. Then, a thin layer of a hydrophilic polymer composition (forming the top coat) is applied. In another embodiment, the hydrophilic polymer coat is applied while the primer coat is still "water wettable or hydrophilic" so as to enhance the adhesion between the primer coat and the top coat. In another embodiment, a middle coat, comprising a mixture of the non-hydrophilic polymer and the hydrophilic polymer compositions, is applied to the primer coat prior to the application of the top coat, so as to improve the adhesion between the top coat and the primer coat. Each coating material is applied such that the loop portions of the coil are coated discretely, without forming a thick layer between the loop portions of the coil. Thus, the flexibility of the coil is retained, yielding a very trackable guide wire. Unlike other coatings on wires that are thicker and/or more brittle, the coating of the devices of present invention is durable and does not break into pieces when flexed, yielding a more flexible but still "slippery tip".

The above summary of the present invention is not intended to describe each illustrated embodiment or every implementation of the present invention. The detailed description that follows particularly exemplifies these embodiments.

DETAILED DESCRIPTION

The present invention pertains to medical devices comprising a coil that are coated, with a multi-layer coating system, to possess the requisite lubricity and flexibility desired in applications where these devices are utilized. The present invention also pertains to a method of coating a medical device comprising a coil to thinly coat portions of the coil with a multi-layer coating system comprising polymeric materials that are non-toxic, not include a cross-linker or any reactive functional groups, and can be easily applied at low temperatures and in an aqueous environment. The medical device comprising a coil is preferably a coiled tip guide wire, or a catheter comprising a coil at its tip or as a portion of its distal section.

The multi-layer coating system comprises a non-hydrophilic polymeric material, as the primer coat, and a hydrophilic polymeric material, as the top coat. The coating system may also comprise a mixture material, as the middle coat, wherein the non-hydrophilic and the hydrophilic polymeric materials are mixed to yield a coating comprising a combination of both polymers. Each of the coating materials is applied to yield a very thin layer such that the resultant coating has a total dry thickness in the range of from about 3 microns to about 30 microns, preferably, about 3 microns to about 15 microns, for a "dual coat" (primer coat and top coat) system, and in the range of from about 5 microns to about 40 microns, preferably, about 8 microns to about 25 microns, for a "tri-coat" (primer coat, middle coat and top coat) system, with the primer coat having a dry thickness in the range of from about 1 micron to about 10 microns, preferably, from about 1 micron to about 5 microns, the top coat having a dry thickness in the range of from about 2 microns to about 20 microns, preferably, from about 2 microns to about 10 microns, and the optional middle coat having a thickness in the range of from about 2 microns to about 10 microns, preferably, from about 5 microns to about 10 microns. The primer coat serves to facilitate the adhesion of the top coat to the medical device or a portion thereof, while the optional middle coat serves to enhance said adhesion.

Each polymeric coat, i.e., the primer coat, the top coat, and optional the middle coat, may comprise one or more layers of the respective polymeric material. In one embodiment of the present invention, one layer of the non-hydrophilic polymer is coated onto the medical device coil, or a portion thereof, forming the primer coat. Then, the primer coat is coated with a layer of the hydrophilic polymer, and the hydrophilic polymer layer is then coated with another layer of hydrophilic polymer, the two layers of the hydrophilic polymer forming the top coat. In another embodiment, the medical device coil, or a portion thereof, is coated with a layer of the non-hydrophilic polymer, which is then coated with another layer of the non-hydrophilic polymer, the two layers of the non-hydrophilic polymer forming the primer coat. Then, two layers of the hydrophilic polymer, that form the top coat, are successively applied to the primer coat. In another embodiment of the present invention, one layer of the non-hydrophilic polymer is coated onto the medical device coil, or a portion thereof. Then, a layer of the mixture of the non-hydrophilic polymer and the hydrophilic polymer is applied to the primer coat, forming the middle coat. Then, two layers of the hydrophilic polymer, that form the top coat, are successively applied to the middle coat. Each layer of each coating material is preferably air dried prior to subsequent layer applications.

The non-hydrophilic and the hydrophilic polymeric coating materials useful in the present invention are those that do not contain any cross-linkers or any reactive functional groups. Suitable non-hydrophilic polymers for use herein include water borne polyurethane dispersions that include Sancure® 1073C (available from Noveon Inc., Sheffield, Ohio) and Bayhydrol® PR-240 (available from Bayer Industrial Chemicals, Pittsburgh, Pa.). The Sancure™ 1073C, a dispersion containing 31% w/w solids in water, is preferred for use herein. It has a specific gravity of 1.08, and a Brookfield viscosity (at 25° C.) of 23 cp. The Bayhydrol™ PR-240 is a dispersion containing 40% w/w solids in water. It has a viscosity (at 25° C.) of 100-500 mPa's.

Suitable hydrophilic polymers for use herein include poly N-vinylpyrrolidone, poly N-vinylpyrrolidone copolymers, carboxymethylcellulose, polyacrylic acid, polyacrylic acid amide (MagnaFloc® 525, available from Ciba Specialty Chemicals PLC, West Yorkshire, GB), cationically-modified hydroxyethylcellulose, polyurethane hydrogel (Tecogel®, available from Noveon Thermedics, Inc., Wilmington, Mass.), polyethylene oxides, polyethylene oxide copolymers, or any combination thereof. The MagnaFloc® 525 is preferred for use herein. It is described by the manufacturer as a low/medium molecular weight polyacrylic acid amide copolymer. MagnaFloc® 525 has a density of 0.8 g/cc, and a viscosity (at 25° C., of 1% solution, with a Fann Viscometer) of 1450 cP at shear rate of 10.22 seconds$^{-1}$.

The suitable polymeric mixture material for use herein is formulated such that the dry weight of the non-hydrophilic polymer comprises from about 10% to about 50% w/w of the dried mixture, and the dry weight of the hydrophilic polymer comprises from about 50% to about 90% of the dried mixture, preferably, the mixture when dried comprises about 50% dry weight of each of the two polymeric materials.

The coating method of the present invention comprises coating a non-hydrophilic polymer onto the surface of at least a portion of a coil of a medical device, and applying a hydrophilic polymer onto the non-hydrophilic polymer layer. The non-hydrophilic polymer is applied as a composition that comprises a non-hydrophilic polymer and water, preferably an aqueous dispersion. The hydrophilic polymer is applied as a composition that may be a solution, a dispersion, or an emulsion, preferably, a solution comprising a hydrophilic polymer and water. For application via dip coating, the non-hydrophilic polymer composition comprises from about 1% to about 5% w/w solids, preferably, from about 2% to about 4% w/w solids, and the hydrophilic polymeric composition solution comprises from about 0.5% to about 2% w/w solids, preferably, about 1% w/w solids. The mixture comprises a combination of the non-hydrophilic polymer and hydrophilic polymer compositions, such that when dried, the non-hydrophilic polymer comprises from about 10% to about 50% w/w of the mixture, and the hydrophilic polymer comprises from about 50% to about 90% w/w of the mixture. For application via spray coating, the solids concentration for a given polymeric composition varies, based on the desired dry coating thickness. Thus, an appropriate composition for each of the coating materials would be prepared for a given spray coating machine or system according to the manufacturer's instructions, based on the desired dry thickness of about 1-10 microns for the primer coat, about 2-10 microns for the optional middle coat, and about 2-20 microns for the top coat, with a maximum total dry thickness of about 30 microns or 40 microns, depending on the coating being a dual-coat or tri-coat system. The term "method" is synonymous with the term "process" for uses herein.

Each layer of the non-hydrophilic polymer composition may be dried prior to the application of the hydrophilic polymer layer. The drying may comprise any suitable drying method, at about 25° C. to about 30° C. (e.g., room temperature), for a period of time in the range of from about 1 to about 5 minutes. The device comprising the multi-layer coating is post baked in an oven for a period of time in the range of from about 4 hours (hrs) to about 6 hrs, preferably for about 6 hrs, at a temperature in the range of from about 50° C. to about 60° C., preferably at about 55° C. The hydrophilic top coat may be dried prior to the post baking, at a temperature in the range of from about 25° C. to about 30° C., for a period of time in the range of from about 1 to about 5 minutes.

Each layer of the coating system may be coated with any coating method known in the art, including dip coating or spray coating. Dip coating and spray coating are particularly well-suited for coating coils. Any machine or system that is capable of applying thin coats of polymeric compositions to coiled devices may be suitable for use herein. Commercially available machines or systems, such as those for dip coating available from DipTech Technologies, Inc. (Cleveland, Ohio), as well as proprietary-designed machines having the requisite functions, may be suitable for use herein. Preferably, the dip coating machine or system comprises a travel arm for attaching the portion of the medical device to be coated. The arm can be programmed via a computer control so as to descend at a given speed and ascend at the same or a different speed, with or without a dwell time in the solution. The system is preferably set up with appropriate stops such that only a given portion of the medical device, e.g., a guide wire tip, is coated. An example of a suitable machine or system for spray coating is the Accu-Mist Ultrasonic Spray system (available from Sono-Tek Corporation, Milton, N.Y.).

When utilizing the dip coating method, each application of a given coating composition comprises dwelling at least a portion of the medical device coil, e.g., the coil tip of a guide wire, in the respective coating composition for up to 5 seconds (sec.), preferably, up to 3 sec. Each application of the coating compositions employs a coating speed of insertion (into the coating composition) in the range of from about 5 inches/minute to about 20 in./min., and a speed of withdrawal (withdrawal from the coating composition) in the range of from about 5 in./min. to about 20 in./min., preferably, about 12 in./min. The thickness of each layer of the coating is directly proportional to the speed of withdrawal.

In one embodiment of the present invention, the distil end of a coiled metal guide wire is coated without rigidifying the guide wire tip. This coating process comprises coating the guide wire tip via dip coating, with a first aqueous coating composition comprising an aliphatic polyester urethane water-borne non-hydrogel dispersion that will form a substantially water insoluble coating layer; this layer being the primer coat. The aliphatic polyester urethane water-borne non-hydrogel dispersion comprises from about 2% to about 5% w/w solids. Then, the primer layer is air dried, and coated, via dip coating, with a second aqueous coating composition comprising a solution of polyacrylic acid amide; this layer being the top coat. The polyacrylic acid amide solution comprises about 1% w/w solids. The resultant coating is very thin, having a total maximum thickness of about 30 microns, with the primer coat having a thickness in the range of from about 1 micron to about 10 microns, and the top coat having a thickness in the range of from about 2 microns to about 20 microns. The multi-layer coating system is formulated so as to not substantially bridge the loop portions of the coil of the guide wire tip, but rather to coat each portion of the coil individually.

It may be advantageous in certain instances to utilize a plasma treatment to enhance adhesion. The plasma treatment is preferably delivered from a Radio Frequency (RF) plasma system containing an oxygen gas (system manufactured by Advanced Plasma Systems, Inc., St. Petersburg, Fla.). In one embodiment of the present invention, the portion of a medical device comprising a coil intended for coating is subjected to a plasma treatment of a standard 10 minute oxygen cycle prior to being coated with a non-hydrophilic polymer composition. In another embodiment, a portion of a coil of a medical device, having been coated with a non-hydrophilic polymer composition, is subjected to a plasma treatment of a standard 10 minute oxygen cycle prior to being coated with a hydrophilic polymer composition. In another embodiment, a portion of a coil of a medical device is subjected to a plasma treatment of a standard 10 minute oxygen cycle prior to being coated with a non-hydrophilic polymer composition, and the portion coated with the non-hydrophilic polymer is subjected to another plasma treatment of a standard 10 minute oxygen cycle prior to being coated with a hydrophilic polymer composition.

In one embodiment of the present invention, the coil of a catheter, or a portion thereof, is coated via the same coating method utilized for the guide wire coil as described above.

In one embodiment of the present invention, the surface of at least a portion of a medical device comprising a coil, comprises a thin coating of a hydrophilic polymer, and a thin coating of a non-hydrophilic polymer therebetween. The medical device or any portion thereof may be fabricated from any material suitable for contact with body fluids or tissue, such as PET, Pebax® (a block copolymer of polyether and polyamide), polyurethane and copolymers thereof, and glass, metal, ceramic, or any combination thereof. Devices fabricated from a metal may comprise a "jacket" or "sleeve", wherein the jacket or sleeve is a polymeric material coated or extruded over the surface of at least a portion of the coil of the device. The polymeric material may be a polyurethane, polyamide, polyester, polyolefin, or Pebax®. The jacket or sleeve serves to provide smoothness and uniformity to the coil surface.

In one embodiment of the present invention, a coiled tip guide wire comprises a non-hydrophilic polymer layer (primer coat) over the tip so that the loops of the coil are able to flex. The surface of said primer coat comprises a hydrophilic polymer layer (top coat) to reduce the friction created by this guide wire as it traverses the lumens in the body. The primer coat adheres to the surface of the guide wire's tip without the use of cross-linking or otherwise reacting with the material from which the guide wire is constructed, such as a metal. The coating, comprising the primer coat and the top coat, of the guide wire tip is very thin (maximum dry thickness of about 30 microns), such that it can be lubricious yet not substantially bridge the loop portions of the coil. The coated guide wire tip is neither stiff nor non-trackable.

The coated medical devices comprising a coil, and the related coating methods of the present invention provide the benefits of ease of navigation, ease of selecting a vessel for entry, ability to navigate into distal anatomy, more tactile feel or control for the physician, and shorter procedure duration. The combination of the above-described multi-layer polymeric coating system and the thin application thereof yields medical device coils possessing the requisite lubricity, flexibility and durability.

The present invention also includes a method of using the medical devices comprising a coil described herein, which comprises the steps of inserting the medical device into a subject's vascular anatomy, guiding the medical device through the subject's anatomy, selecting the vessel for treatment, and positioning the medical device in the targeted area of the vessel. In applications where the medical device comprising a coil is a guide wire having a coated coil tip, the guide wire may be inserted into a catheter to facilitate access to the subject's vascular anatomy.

EXAMPLES

Having generally described the invention, a more complete understanding thereof may be obtained by reference to the following examples that are provided for purposes of illustration only and do not limit the invention.

Example 1

A first coating composition, intended as the primer coat, was prepared by adding the following ingredients to a 500 cc glass beaker while stirring for 15 minutes:
 15 grams of a 30% w/w dispersion of Sancure® 1073C
 100 grams of distilled water This first coating composition was poured into a 250 cc glass jar, such that the jar was 15 cm full with the coating composition.

A second coating composition, intended as the top coat, was prepared by adding the following ingredients to a 1000 cc glass beaker and stirring with a powered propeller stirrer for 6 hours until the polymer dissolved.

10 grams of MagnaFloc® 525
990 grams of distilled water

When the polymer was dissolved, the second coating composition was poured into a 250 cc glass jar, such that the jar was 15 cm full with the coating composition.

A 0.014 in. coronary guide wire with a coiled tip was fixtured to enable the dipping of 15 cm of the coiled tip. The tip of the guide wire was dipped into the first coating composition at a speed of 12 in./min., and withdrawn at a speed of 12 in./min. The coated guide wire tip was air dried for 5 minutes. Then, it was dipped into the second coating composition at a speed of 12 in./min and withdrawn at a speed of 12 in./min, and air dried for 5 minutes. The coated guide wire was then post baked in an oven for about 6 hours at a temperature of about 55° C.

The device coated per Example 1 showed good adhesion between the surface of the device and the primer coat, as well as between the primer coat and the top coat. The coating of the guide wire tip was evaluated by traversing the guide wire through a 6f catheter in a torture track simulating the coronary artery. The catheter was filled with saline. The 0.014 in. guide wire, having a tip coated as described in Example 1, was traversed through the catheter; and it easily navigated the curve into the ostium and maneuvered into the right coronary artery. The same 0.014 in. guide wire, but with an uncoated, tip was also traversed through the catheter; however, it had difficulty navigating the bend into the ostium and gaining access to the targeted coronary artery. Each of the coated and the uncoated guide wire tips were rubbed between two gloved fingers to qualitatively determine their lubricity. The coated guide wire tip was more slippery as compared to the uncoated wire tip.

Example 2

The coiled tip of a 0.014 in. guide wire was exposed to a standard 10 minute RF oxygen cycle plasma treatment prior to being coated and evaluated as described in Example 1.

Example 3

The coiled tip of a 0.014 in. guide wire coated with the first coating composition and dried as described in Example 1. Then, the coated guide wire tip was exposed to a standard 10 minute RF oxygen cycle plasma treatment prior to being coated with the second coating composition, dried, and evaluated as described in Example 1.

The devices coated and evaluated per Example 2 and Example 3 showed good adhesion between the surface of the device and the primer coat, as well as between the primer coat and the top coat. They also provided the same level of navigation ease and slipperiness as the coated device of Example 1. The result of these evaluations confirm that medical devices comprising a coil, such as a coiled tip guide wire, coated thinly and in the manner described hereinabove with the multi-layer coating system provide desired flexibility, lubricity and trackability.

As noted above, the present invention pertains to medial devices comprising a coil, such as guide wires and catheters, coated with non cross-linked, thin and flexible aqueous coatings, and methods related thereto. The present invention should not be considered limited to the particular embodiments described above, but rather should be understood to cover all aspects of the invention as fairly set out in the appended claims. Various modifications, equivalent processes, as well as numerous structures to which the present invention may be applicable will be readily apparent to those skilled in the art to which the present invention is directed upon review of the present specification. The claims are intended to cover such modifications.

I claim:

1. A method for applying a multi-layer lubricious coating to a surface of a medical device comprising a coil, comprising the steps of:
   a) applying to the surface of at least a portion of the coil of the medical device comprising a coil, at least one layer of an aqueous non-hydrophilic polymer dispersion capable of adhering to said surface and providing a total dry coating thickness in the range of about 1 micron to about 10 microns; and
   b) applying, to the at least one layer of an aqueous non-hydrophilic polymer dispersion, at least one layer of an aqueous hydrophilic polymer composition capable of adhering to the at least one layer of an aqueous non-hydrophilic polymer dispersion and providing a total dry coating thickness in the range of about 2 microns to about 20 microns,
   said aqueous non-hydrophilic polymer dispersion or said aqueous hydrophilic polymer composition being free from any cross-linkers,
   said aqueous non-hydrophilic polymer dispersion or said aqueous hydrophilic polymer composition being applied via a dip coating, spray coating, painting or pad coating technique,
   said multi-layer coating not substantially bridging the space between the successive loop portions of the device coil.

2. A method according to claim 1, comprising the step of applying, to the at least one layer of an aqueous non-hydrophilic polymer dispersion, at least one layer of a mixture composition, said mixture composition comprising an aqueous non-hydrophilic polymer dispersion and an aqueous hydrophilic polymer composition, capable of adhering to the at least one layer of an aqueous non-hydrophilic polymer dispersion and to the at least one layer of an aqueous hydrophilic polymer composition, and providing a total dry coating thickness in the range of about 2 microns to about 10 microns.

3. A method according to claim 2, comprising the step of drying the at least one layer of an aqueous non-hydrophilic polymer dispersion prior to the step of applying at least one layer of a mixture composition.

4. A method according to claim 3, comprising the step of drying the at least one layer of a mixture composition prior to the step of applying at least one layer of an aqueous hydrophilic polymer composition.

5. A method according to claim 1, comprising the step of drying the at least one layer of an aqueous non-hydrophilic polymer dispersion prior to the step of applying at least one layer of an aqueous hydrophilic polymer composition.

6. A method according to claim 1, comprising the step of post-baking the a coil coated with the at least one layer of an aqueous hydrophilic polymer composition.

7. A method according to claim 1, said aqueous non-hydrophilic polymer dispersion being an aqueous polyurethane dispersion.

8. A method according to claim 1, said aqueous non-hydrophilic polymer dispersion comprising from about 1% to about 5% w/w solids.

9. A method according to claim 1, said aqueous hydrophilic polymer composition being a solution, a dispersion, or an emulsion, said solution, dispersion, or emulsion comprising poly N-vinylpyrrolidone, poly N-vinylpyrrolidone copolymers, carboxymethylcellulose, polyacrylic acid, polyacrylic acid amide, polyurethane hydrogel, cationically-modified hydroxyethylcellulose, polyethylene oxides, polyethylene oxide copolymers, or any combination thereof.

10. A method according to claim 9, said aqueous hydrophilic polymer composition being a solution comprising from about 1% to about 5% w/w solids.

11. A method according to claim 1, said dip coating utilizing a speed of insertion in the range of from about 5 in./min. to about 20 in./min., and a speed of withdrawal in the range of from about 5 in./min. to about 20 in./min.

12. A method for applying a multi-layer lubricious coating to the surface of a medical device comprising a coil, comprising the steps of:

a) applying, to the surface of at least a portion of the coil of a medical device comprising a coil, at least one layer of an aqueous non-hydrophilic polymer composition capable of adhering to said surface and providing a total dry coating thickness in the range of about 1 micron to about 10 microns;

b) drying the at least one layer of an aqueous non-hydrophilic polymer composition;

c) applying, to the dried at least one layer of an aqueous non-hydrophilic polymer composition, at least one layer of an aqueous hydrophilic polymer composition capable of adhering to the at least one layer of an aqueous non-hydrophilic polymer composition and providing a total dry coating thickness in the range of about 2 microns to about 20 microns, d) subjecting to a RF oxygen plasma treatment: (i) the surface of at least a portion of the coil, prior to the applying at least one layer of an aqueous non-hydrophilic polymer composition, (ii) the surface of the dried at least one layer of an aqueous non-hydrophilic polymer composition, prior to the applying at least one layer of an aqueous hydrophilic polymer composition, or (iii) both i) and ii), said aqueous non-hydrophilic polymer composition or said aqueous hydrophilic polymer composition being applied via a dip coating, spray coating, painting or pad coating technique, and said multi-layer coating not substantially bridging the space between the successive loop portions of device coil.

* * * * *